United States Patent
Takahashi et al.

(10) Patent No.: US 9,612,214 B2
(45) Date of Patent: Apr. 4, 2017

(54) X-RAY FLUORESCENCE ANALYZER

(71) Applicant: HITACHI HIGH-TECH SCIENCE CORPORATION, Minato-ku, Tokyo (JP)

(72) Inventors: Haruo Takahashi, Tokyo (JP); Ryusuke Hirose, Tokyo (JP); Isao Yagi, Tokyo (JP); Toshiyuki Takahara, Tokyo (JP)

(73) Assignee: HITACHI HIGH-TECH SCIENCE CORPORATION, Tokyo (JP)

(*) Notice: Subject to any disclaimer, the term of this patent is extended or adjusted under 35 U.S.C. 154(b) by 0 days.

(21) Appl. No.: 14/735,393

(22) Filed: Jun. 10, 2015

(65) Prior Publication Data
US 2015/0362445 A1 Dec. 17, 2015

(30) Foreign Application Priority Data
Jun. 13, 2014 (JP) .................................. 2014-135066

(51) Int. Cl.
*G01N 23/223* (2006.01)
*G01N 35/00* (2006.01)
*G21K 1/06* (2006.01)

(52) U.S. Cl.
CPC ..... *G01N 23/223* (2013.01); *G01N 35/00693* (2013.01); *G21K 1/067* (2013.01)

(58) Field of Classification Search
USPC ....................................................... 378/44
See application file for complete search history.

(56) References Cited

U.S. PATENT DOCUMENTS

| 5,060,247 A | * | 10/1991 | Watanabe | .............. G01B 15/02 378/148 |
| 5,060,320 A | * | 10/1991 | Sargent | .................... E03D 5/08 4/249 |
| 6,345,086 B1 | * | 2/2002 | Ferrandino | .......... G01N 23/223 378/206 |
| 2014/0268133 A1 | * | 9/2014 | McManus | ............... G01J 3/443 356/316 |

FOREIGN PATENT DOCUMENTS

JP 59-67449 A 4/1984

* cited by examiner

*Primary Examiner* — Phillip A Johnston
(74) *Attorney, Agent, or Firm* — Brinks Gilson & Lione

(57) ABSTRACT

An X-ray fluorescence analyzer includes: a measurement device having: an X-ray source that emits an X-ray; an irradiation area restricting member that restricts an area of a measurement sample to be irradiated with the X-ray as a primary X-ray; and a detector that detects a secondary X-ray generated from the measurement sample. The analyzer further includes: a sample stage that holds and moves the measurement sample between a measurement position at which the measurement sample is irradiated with the primary X-ray to detect the secondary X-ray by the detector and a first retracted position at which the measurement sample is retracted from the measurement position; and a calibration sample moving mechanism that holds a calibration sample for calibrating the measurement device and moves the calibration sample between the measurement position and a second retracted position at which the calibration sample is retracted from the measurement position.

7 Claims, 2 Drawing Sheets

X-RAY FLUORESCENCE ANALYZER

CROSS-REFERENCE TO RELATED APPLICATION

This application claims priority from Japanese Patent Application No. 2014-135066, filed on Jun. 13, 2014, the entire subject matter of which is incorporated herein by reference.

BACKGROUND

1. Technical Field

The present disclosure relates to an X-ray fluorescence analyzer.

2. Description of the Related Art

X-ray fluorescence analysis is a technique of irradiating a sample with an X ray emitted from an X-ray source, and detecting fluorescent X-rays emitted from the sample by an X-ray detector, and performing qualitative analysis of the sample or quantitative analysis of a concentration, a film thickness, or the like based on the intensities of the fluorescent X-rays.

The constituent elements of the sample generate fluorescent X-rays having energies characteristic of the individual elements. Therefore, the spectra of the measured X rays are searched for peaks of the fluorescent X-rays characteristic of the individual elements, whereby it is possible to find out which elements are contained. This analysis is called qualitative analysis.

Meanwhile, quantitative analysis uses a fact that the intensity of the fluorescent X-ray of each constituent element which is obtained is determined by the relation between the state of the X ray with which a sample is irradiated and the amount of the corresponding element existing in the irradiation area. Specifically, first, a sample is irradiated with X rays having known X-ray states, that is, known X-ray intensities for each energy, and the intensities of fluorescent X-rays of individual elements generated as the results of the irradiation is measured, and then the amounts of the elements capable of making X rays with those intensities be generated is calculated.

In this calculation process, various methods are used. In every method, for the accuracy of the analysis, it is important that the amount and energy distribution of X-ray for irradiation matches with the premise of calculation. In concentration analysis, it is possible to cancel the influence to a certain extent in a case where the entire intensity increases while the energy distribution is kept. However, in film thickness calculation, it is difficult to distinguish between increase or decrease in intensity and increase or decrease in film thickness, and thus the influence of variation in X ray for irradiation is more serious.

Since it is practically almost impossible to prepare an X-ray irradiation system which is completely stable and has a precisely defined energy distribution, a technique of measuring a sample having a known composition and a known structure and calibrating a device using the intensity of an X ray obtained from the measurement is generally used. Therefore, device calibration is a very important technique for accurate quantitative analysis and being required to be performed routinely and accurately. Due to this request, there has been disclosed a configuration in which a sample for calibration is mounted on a shutter member and automatically performs calibration. An example of such configuration is disclosed in Japanese patent publication No. JP-A-S59(1984)-067449.

In X-ray fluorescence analysis, the size of an area to be measured is often to be one of major concerns. In general, the measurement area is defined by restricting an X-ray irradiation area. According to the sizes of samples which are measurement targets, various devices having irradiation areas in the order of several millimeter to several tens micrometer are provided. Among those devices, devices having particularly small irradiation areas use advanced technologies of a collimator which is a structure capable of blocking X rays and having tiny holes, a capillary X-ray optical element for focusing X rays on a tiny area by using a total reflection phenomenon of the inner surface of a hollow glass fiber, and the like.

It is known that a misalignment in the positional relation between a collimator or capillary X-ray optical element and an X-ray generator influences the intensities and energy distributions of X rays to be emitted. That is, it can be said that the positional relation of the constituent elements of each of those devices is an element which should be calibrated to have accurate quantitative analysis.

The configuration disclosed in the Japanese patent publication No. JP-A-S59(1984)-067449 allows to move a calibration sample mounted on a shutter member into an X-ray irradiation area, and calibrate intensity variation attributable to variation of an X-ray source for irradiation with an X ray, but the route of the X ray and the incident direction of the X ray to a detector are different from those of normal measurement. For this reason, there may be a problem that, in the strict sense, a measurement condition for calibration is different from a normal measurement condition, and it is not possible to calibrate variations attributable to every element.

Further, in devices using X-ray focusing elements such as poly-capillaries recently being in widespread use, a small position gap between a focusing element and an X-ray generating portion of an X-ray source is attributable to intensity variation, even if these mechanisms are disposed above the focusing element, device calibration inevitably may become incomplete.

Furthermore, in general, in order to reduce an X-ray irradiation area, it is preferable to reduce a distance between a focusing element and a sample. Therefore, it may be difficult to dispose a calibration below the focusing element.

For these reasons, devices using X-ray focusing elements may have a problem that they do not have means for automatically calibrating the devices.

SUMMARY

The present disclosure has been made in view of the above-described circumstances, and one of objects of the present disclosure is to provide an improved X-ray fluorescence analyzer.

According to an exemplary embodiment of the present disclosure, there is provided an X-ray fluorescence analyzer including: an X-ray source; an irradiation area restricting member that restricts an area of a measurement sample to be irradiated with an X ray emitted as a primary X-ray from the X-ray source; a detector that detects a secondary X-ray generated from the measurement sample; a calibration sample for calibrating a device including the X-ray source, the irradiation area restricting member, and the detector; a sample stage on which the measurement sample is mounted, the sample stage arranging the measurement sample at a position in which a surface of the measurement sample faces the irradiation area restricting member with a predetermined distance from the irradiation area restricting member on an irradiation axis of the primary X-ray; and a calibration sample moving mechanism that holding the calibration sample and moving the calibration sample between a retraction position which is an arbitrary position deviated from a route of the primary X-ray and a spatial position that is the same with an irradiation position of the primary X-ray on the surface of the measurement sample spaced apart from the irradiation area restricting member by the predetermined distance, the calibration sample moving mechanism being configured to be independent from the sample stage.

According to another exemplary embodiment of the present disclosure, there is provided an X-ray fluorescence analyzer including: a measurement device having: an X-ray source that emits an X-ray; an irradiation area restricting member that restricts an area of a measurement sample to be irradiated with the X-ray as a primary X-ray; and a detector that detects a secondary X-ray generated from the measurement sample by being irradiated with the primary X-ray. The X-ray fluorescence analyzer further includes: a sample stage that holds and moves the measurement sample between a measurement position at which the measurement sample is irradiated with the primary X-ray to detect the secondary X-ray by the detector and a first retracted position at which the measurement sample is retracted from the measurement position; and a calibration sample moving mechanism that holds a calibration sample for calibrating the measurement device and moves the calibration sample between the measurement position and a second retracted position at which the calibration sample is retracted from the measurement position.

BRIEF DESCRIPTION OF THE DRAWINGS

The above and other aspects of the present disclosure will become more apparent and more readily appreciated from the following description of illustrative embodiments of the present disclosure taken in conjunction with the attached drawings, in which.

DETAILED DESCRIPTION

Hereinafter, an embodiment of an X-ray fluorescence analyzer according to the present disclosure will be described with reference to FIGS. 1 and 2.

Figure 1:
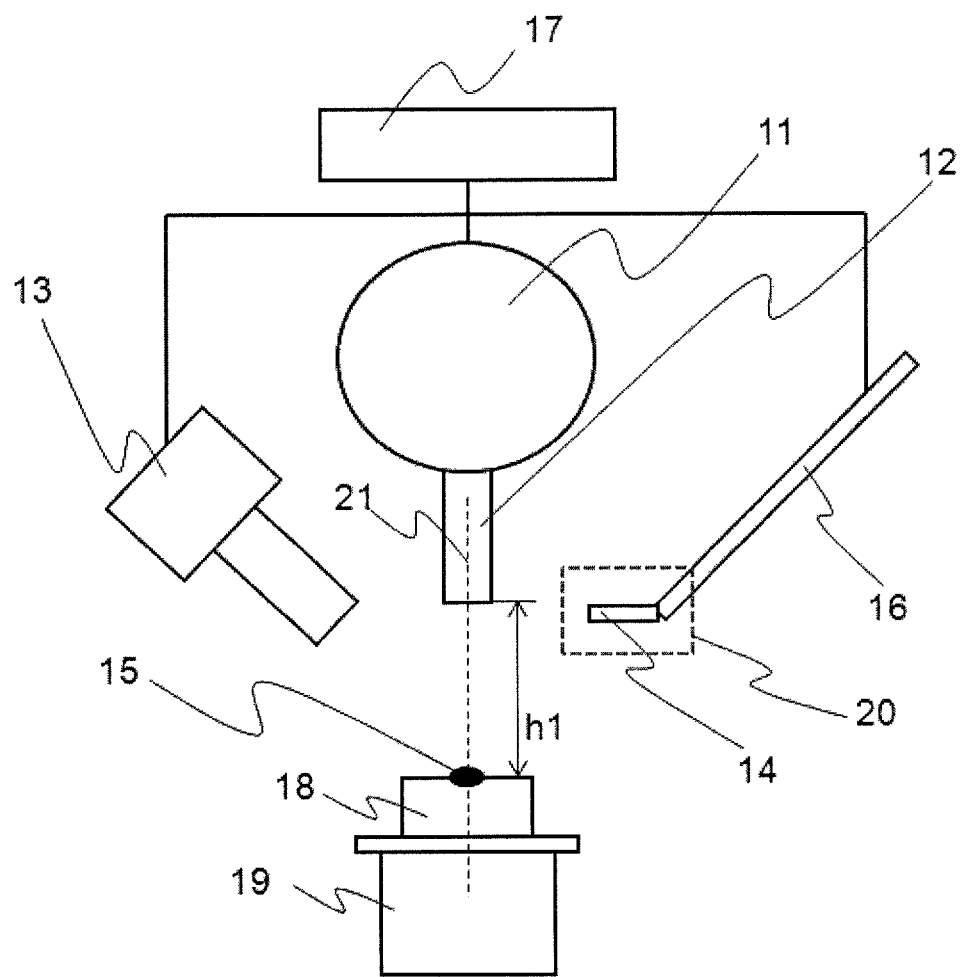
FIG. 1 is an overall configuration diagram illustrating an embodiment of an X-ray fluorescence analyzer according to the present disclosure.

As shown in FIG. 1, an X-ray fluorescence analyzer 1 according to the present embodiment includes an X-ray source 11, an irradiation area restricting member 12, a detector 13, a calibration sample moving mechanism 16, and a sample stage 19.

As the X-ray source 11, a versatile X-ray tube universal for X-ray fluorescence analyzers being generally sold may be used.

As the irradiation area restricting member 12, a poly-capillary may be used. In a case where an irradiation diameter is fixed, poly-capillaries can perform irradiation with X rays having higher intensities as compared to collimators which restrict X-ray irradiation areas by simple apertures. Therefore, use of poly-capillaries in cases where high-accuracy measurements are required is increasing. In situations where high-accuracy measurements are required, there are high requirements with respect to device calibration. Therefore, those situations are suitable as examples to which the present disclosure is applied.

The detector 13 is configured by a detection element, a pre-amplifier, a digital pulse height analyzer, and a spectrum memory. In response to incidence of an X ray, the detection element generates electric charge proportional to the energy of the X ray. The generated electric charge is output as a voltage signal through the pre-amplifier, and the digital pulse height analyzer converts the voltage signal output from the pre-amplifier into a sequence of digital values arranged in chronological order, and calculates the incidence timing and energy of the X ray. If X ray incidence is detected, a channel count value of the spectrum memory corresponding to the calculated energy is added.

The spectrum memory is cleared when measurement starts, and when measurement finishes, addition into the spectrum memory is stopped. In the present embodiment, since the intensity of the output of the poly-capillary is high, as a detection element which is unlike to be saturated before a counting rate becomes high, a semiconductor drift type detector is used.

As a calibration sample 14, various samples can be used as long as their compositions and structures are known. In the present embodiment, a zirconium plate is used. Based on the intensity of a fluorescent X-ray which is generated from zirconium, variation in the intensity is calibrated, and based on the position of a peak of the fluorescent X-ray of zirconium, the relation between the channel of the spectrum memory and energy is calibrated.

When calibration is required, the calibration sample moving mechanism 16 avoids interference between a measurement sample 8 and the calibration sample 14 while moving the calibration sample 14 such that the calibration sample 14 is disposed at the position of a primary X-ray irradiation position 15 of the measurement sample 18. Therefore, the calibration sample moving mechanism 16 is attached to the calibration sample moving mechanism 16.

Subsequently, an operation related to an actual configuration will be described.

The calibration sample moving mechanism 16 is configured using a linearly movable mechanism, a rotation mechanism (not shown), and the like, so as to be able to move the calibration sample 14 between differentiation learning function two different positions, that is, a retraction position and a measurement position. The two positions are a primary X-ray irradiation position 15 which is on a primary X-ray irradiation axis 21 which is configured by the X-ray source 11 and the irradiation area restricting member 12, and a retraction position 20 which is not irradiated with an X ray. Normally, the calibration sample 14 is disposed at the retraction position 20. Also, the calibration sample moving mechanism 16 is provided so as to be structurally independent from the sample stage 19. Therefore, the operable range of the calibration sample moving mechanism is not influenced by the shape of a sample 18 being on the sample stage 19.

The sample stage 19 has a structure to be used with a sample 18 as a measurement target, which is mounted on the sample stage 19. The sample stage 19 is driven along three axes perpendicular to one another, that is, X, Y, and Z axes. One axis of the three axes is disposed substantially parallel to the primary X-ray irradiation axis 21. Adjustment of the position of a sample 18 first needs movement in a plane perpendicular to the primary X-ray irradiation axis 21 such that a desired position of the sample can be irradiated with a primary X-ray.

Further, movement in the direction of the primary X-ray irradiation axis 21 influences the irradiation area size and irradiation intensity of the primary X-ray and the sensitivity of detection of a secondary X-ray generated. For this reason, the primary X-ray irradiation position 15 is always adjusted such that the surface (measurement target portion) of the measurement sample 18 keeps constant distances (heights) from the irradiation area restricting member 12 and the detector 13.

Figure 2:
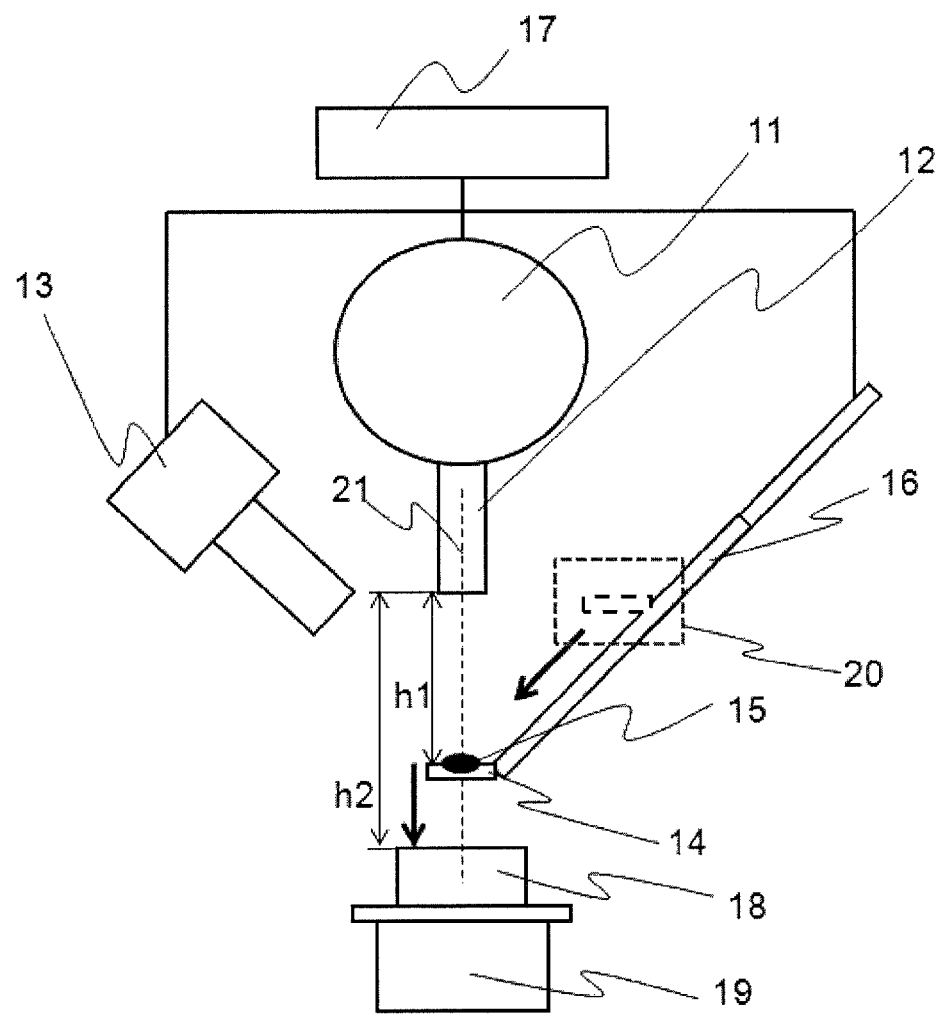
FIG. 2 is another overall configuration diagram illustrating the embodiment of the X-ray fluorescence analyzer according to the present disclosure.

As shown in FIGS. 1 and 2, since the positions of the irradiation area restricting member 12 and the detector 13 are fixed, the primary X-ray irradiation position 15 can be determined only by specifying the position of the height h1 of the lower surface of the irradiation area restricting member 12 from the upper surface of the measurement sample 18. Therefore, the primary X-ray irradiation position 15 is a position specified in a three dimensional space.

In a case of moving the calibration sample 14 to the primary X-ray irradiation position 15 as described above in order to perform calibration, it is confirmed that the calibration sample 14 will not collide with the measurement sample 18. If necessary, the sample stage 19 is operated to retract the measurement sample 18. As shown in FIG. 2, the retraction position is arbitrarily specified according to the distance (height) h2 of the upper surface of the measurement sample 18 from the lower surface of the irradiation area restricting member 12 which does not collide with the calibration sample 14 in a case where the measurement sample 18 is moved by the calibration sample moving mechanism 16.

Next, the calibration sample moving mechanism 16 is operated, whereby the calibration sample 14 is moved to the primary X-ray irradiation position 15 which is the position of the distance (height) h1 from the lower surface of the irradiation area restricting member 12. By doing this, the calibration sample 14 can be irradiated with the primary X-ray in the substantially same condition as that during measurement of the measurement sample 18. Therefore, if the detector 13 is instructed to start, the spectrum of the calibration sample 14 according to the substantially same condition as that during measurement of the measurement sample 18 is integrated in the spectrum memory. If a predetermined measurement time comes, the measurement is finished, and the spectrum of the calibration sample 14 is obtained.

From this spectrum, the intensity of the fluorescent X-ray of zirconium which is a calibration element is read. Then, based on the magnitude of the intensity, the sensitivity of the spectrometer is calibrated. After the measurement for calibration, the calibration sample moving mechanism 16 is operated again, whereby the calibration sample 14 is moved to the retraction position 20 again, and then the calibration operation finishes.

In addition to the embodiment described until now, a controller 17 capable of controlling the X-ray source 11, the detector 13, and the calibration sample moving mechanism 16 may be provided, whereby it is possible to automatically perform an operation necessary for calibration. For example, the controller can be programmed so as to perform calibration at predetermined time intervals, whereby it is possible to always the fluorescent X-rays in a good state.

In a case of automatically performing calibration, it is required to avoid collision with the measurement sample 18 placed on the sample stage 19.

Specifically, the controller 17 is programmed to operate the calibration sample moving mechanism 16, whereby the calibration sample 14 is moved from the calibration sample retraction position 20 to the primary X-ray irradiation position 15, while checking whether the measurement sample 18 is at the primary X-ray irradiation position 15, and automatically retract the sample stage 19 to a safe position (the distance (height) h2 of the upper surface of the measurement sample 18 from the lower surface of the irradiation area restricting member 12) in a case of determining that the calibration sample 14 would collide with the measurement sample 18. Thereafter, a calibration operation is automatically performed, and then the sample stage 19 is returned to the original position.

In the embodiment described here, the sample stage 19 movable along three axes perpendicular to one another is used. However, methods of vertically moving the whole of a structure including the sample stage for moving a sample along two axes in a horizontal plane, the X-ray source 11, the irradiation area restricting member 12, the detector 13, and the calibration sample moving mechanism 16, thereby adjusting the distance from the sample 18, can be considered. These methods are also included in the disclosure range of the present disclosure.

Also, in the embodiment, in order to describe a specific operation, with respect to the individual constituent elements, specific examples have been given and described. However, forms to be used as the X-ray source 11, the irradiation area restricting member 12, the detector 13, and the sample stage 19 does not influence defining of the present disclosure. Also, even with respect to which kind of calibration information to be calculated from the material of the calibration sample 14 and the spectrum obtained from the calibration sample, various modifications are possible mounting of the spectrometer.

As described with reference to the exemplary embodiment, according to a first mode of the present disclosure, there is provided an X-ray fluorescence analyzer including: an X-ray source; an irradiation area restricting member that restricts an area of a measurement sample to be irradiated with an X ray emitted as a primary X-ray from the X-ray source; a detector that detects a secondary X-ray generated from the measurement sample; a calibration sample for calibrating a device including the X-ray source, the irradiation area restricting member, and the detector; a sample stage on which the measurement sample is mounted, the sample stage arranging the measurement sample at a position in which a surface of the measurement sample faces the irradiation area restricting member with a predetermined distance from the irradiation area restricting member on an irradiation axis of the primary X-ray; and a calibration sample moving mechanism that holding the calibration sample and moving the calibration sample between a retraction position which is an arbitrary position deviated from a route of the primary X-ray and a spatial position that is the same with an irradiation position of the primary X-ray on the surface of the measurement sample spaced apart from the irradiation area restricting member by the predetermined distance, the calibration sample moving mechanism being configured to be independent from the sample stage.

According to this configuration, it is possible to irradiate a calibration sample with an X ray having passed through all components through which an X ray needs to pass until a normal measurement sample is irradiated with the X ray, and the way how the influence of variation of the spectrometer appears in the result of measurement of the calibration sample and the way how the influence of variation of the spectrometer appears in the result of measurement of a normal measurement sample become very similar. Therefore, accurate and precise spectrometer calibration becomes possible.

According to a second mode of the present disclosure, the X-ray fluorescence analyzer according to the first mode may further include: a controller that controls the X-ray source, the detector, and the calibration sample moving mechanism; and an automatic device calibrator that operates the calibration sample moving mechanism to move the calibration sample to the spatial position that is same with the primary X-ray irradiation position of the measurement sample, and operates the detector to detect a secondary X-ray which is generated by irradiating the calibration sample with the X ray emitted from the irradiation area restricting member, and automatically calibrates the device based on a result of detection f the secondary X-ray.

According to this configuration, it is possible to automatically perform a procedure from calibration sample disposition to calibration measurement, and the spectrometer can keep a correctly calibrated state, without making a user do special work.

According to a third mode of the present disclosure, in the X-ray fluorescence analyzer according to the second mode, the sample stage may be provided with a sample stage moving mechanism that moves in at least one direction of a three-dimensional directions of X, Y, and Z directions, and the controller may control the sample stage moving mechanism to retract the measurement sample to a position where the calibration sample does not interfere with the measurement sample before operating the calibration sample moving mechanism.

According to this configuration, due to automation of calibration, it is possible to move the calibration sample and the measurement sample without interference between them, and it is possible to realize stable measurement over a long time.

According to the X-ray fluorescence analyzer having the above described configuration, before normal measurement or at arbitrary intervals in the course of measurement, it is possible to automatically irradiate the calibration sample with an X ray emitted from a focusing element such as a collimator or a poly-capillary under the almost same condition as a normal sample measurement condition, thereby calibrating the spectrometer. Therefore, it is possible to perform long-term unattended measurement while performing accurate calibration, and significant improvement of work efficiency becomes possible without degrading measurement accuracy.

What is claimed is:

1. An X-ray fluorescence analyzer comprising:
  an X-ray source;
  an irradiation area restricting member that restricts an area of a measurement sample to be irradiated with an X ray emitted as a primary X-ray from the X-ray source;
  a detector that detects a secondary X-ray generated from the measurement sample;
  a calibration sample for calibrating a device including the X-ray source, the irradiation area restricting member, and the detector;
  a sample stage on which the measurement sample is mounted, the sample stage arranging the measurement sample at a position in which a surface of the measurement sample faces the irradiation area restricting member with a predetermined distance from the irradiation area restricting member on an irradiation axis of the primary X-ray; and
  a calibration sample moving mechanism including holding the calibration sample at a retraction position which is an arbitrary position deviated from a route of the primary X-ray and a spatial position during sample measurement, and moving the calibration sample from the retraction position to a same irradiation position of the measurement sample having a same predetermined irradiation distance by the primary X-ray which separates the measurement sample from the irradiation area restricting member, wherein the calibration sample moving mechanism being configured to be independent from the sample stage.

2. The X-ray fluorescence analyzer according to claim 1 further comprising:
  a controller that controls the X-ray source, the detector, and the calibration sample moving mechanism; and
  an automatic device calibrator that operates the calibration sample moving mechanism to move the calibration sample to the spatial position that is same with the primary X-ray irradiation position of the measurement sample, and operates the detector to detect a secondary X-ray which is generated by irradiating the calibration sample with the X ray emitted from the irradiation area restricting member, and automatically calibrates the device based on a result of detection f the secondary X-ray.

3. The X-ray fluorescence analyzer according to claim 2, wherein the sample stage is provided with a sample stage moving mechanism that moves in at least one direction of a three-dimensional directions of X, Y, and Z directions, and
  wherein the controller controls the sample stage moving mechanism to retract the measurement sample to a position where the calibration sample does not interfere with the measurement sample before operating the calibration sample moving mechanism.

4. The X-ray fluorescence analyzer according to claim 1, wherein: the irradiation area restricting member is provided with a collimator.

5. The X-ray fluorescence analyzer according to claim 1, wherein the irradiation area restricting member is provided with a poly-capillary.

6. The X-ray fluorescence analyzer according to claim 1, wherein the irradiation area restricting member is provided with a mono-capillary.

7. An X-ray fluorescence analyzer having a measurement device, comprising:
  an X-ray source that irradiates X-ray;
  an irradiation area restricting member that restricts an area of a measurement sample to be irradiated with the X-ray as a primary X-ray; and
  a detector that detects a secondary X-ray generated from the measurement sample by being irradiated with the primary X-ray;
  a sample stage that holds and moves the measurement sample between a measurement position at which the measurement sample is irradiated with the primary X-ray and a first retracted position at which the measurement sample is retracted away from the measurement position during calibration; and
  a calibration sample moving mechanism that holds a calibration sample at a second retraction position which is an arbitrary position retracted from the measurement position during sample measurement, such that during calibration, the calibration sample is moved from the second retraction position to a same irradiation position of the measurement sample having a same predetermined irradiation distance by the primary X-ray which separates the measurement sample from the irradiation area restricting member.

* * * * *